United States Patent [19]

Jeffries, Jr. et al.

[11] Patent Number: 4,782,226
[45] Date of Patent: Nov. 1, 1988

[54] OPTOELECTRONIC CHEMICAL REACTION DETECTOR

[75] Inventors: Martin F. Jeffries, Jr., San Jose; Edward Kulha, Santa Clara, both of Calif.

[73] Assignee: Semi-Gas Systems, Inc., San Jose, Calif.

[21] Appl. No.: 69,763

[22] Filed: Jul. 6, 1987

[51] Int. Cl.$^4$ .............................................. H01J 5/16
[52] U.S. Cl. ..................................... 250/227; 350/96.1
[58] Field of Search ................ 250/574, 575, 227; 350/96, 96.1

[56] References Cited

U.S. PATENT DOCUMENTS

| 3,906,241 | 9/1979 | Thompson | 250/575 |
| 4,152,075 | 5/1979 | Rellstab et al. | 250/575 |
| 4,358,960 | 11/1982 | Porter | 250/227 |
| 4,564,755 | 1/1986 | Winzer et al. | 250/227 |
| 4,591,711 | 5/1986 | Taumberger | 250/227 |
| 4,591,712 | 5/1986 | Thalman | 250/227 |

Primary Examiner—David C. Nelms
Assistant Examiner—Jessica Ruoff
Attorney, Agent, or Firm—Thomas E. Schatzel

[57] ABSTRACT

A tube is attached inside a container and forms an inlet aperture. A transparent bulb is sealed over the end of the tube. A fiber optic probe is inserted into the tube and bulb. The fiber optic probe is connected to a fiber optic transmitter and receiver, which sends a beam of light down the probe. The beam of light reflects off the contents of the container and the reflected light is received by the fiber optic probe. The fiber optic transmitter and receiver compares the light intensity of the reflected light with the light intensity of the light beam. Changes in this radio indicate there has been a change in the contents of the container.

15 Claims, 2 Drawing Sheets

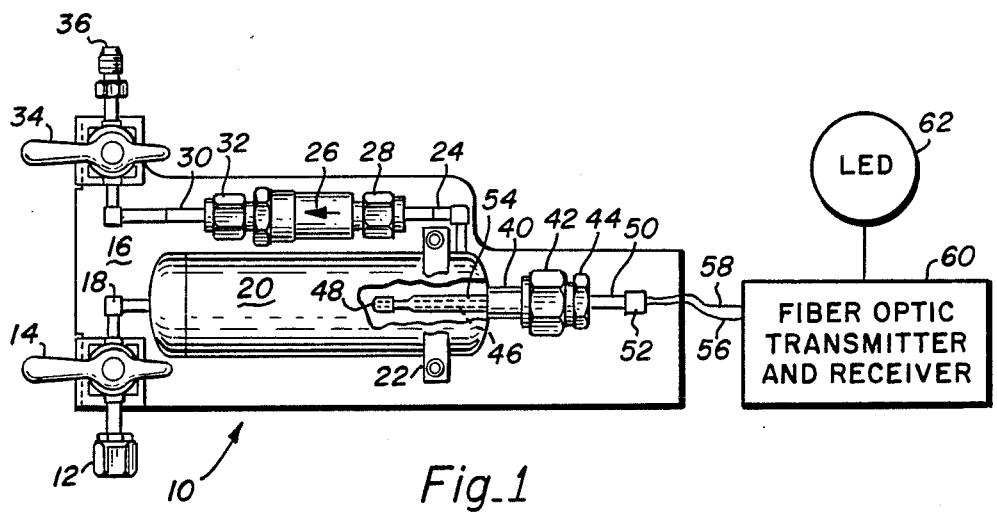
Fig_1
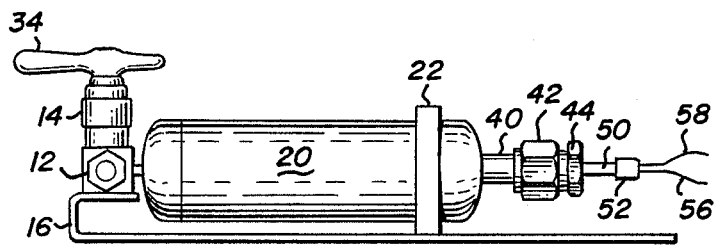
Fig_2
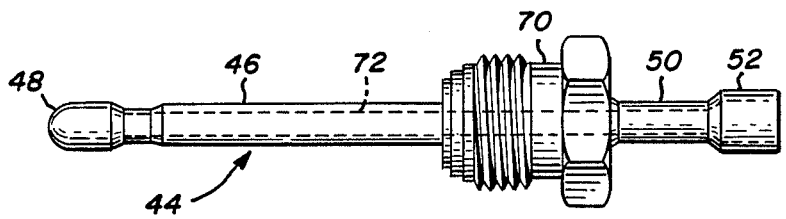
Fig_3
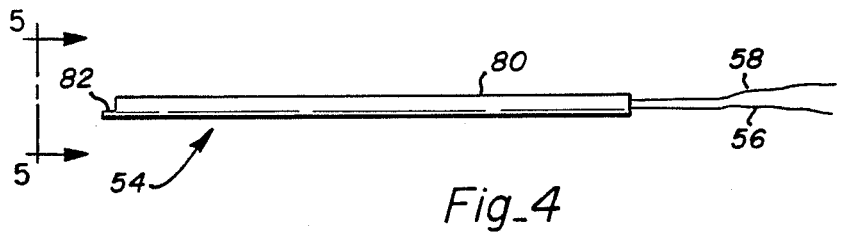
Fig_4

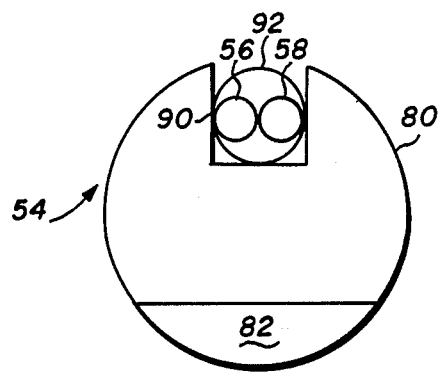
Fig_5
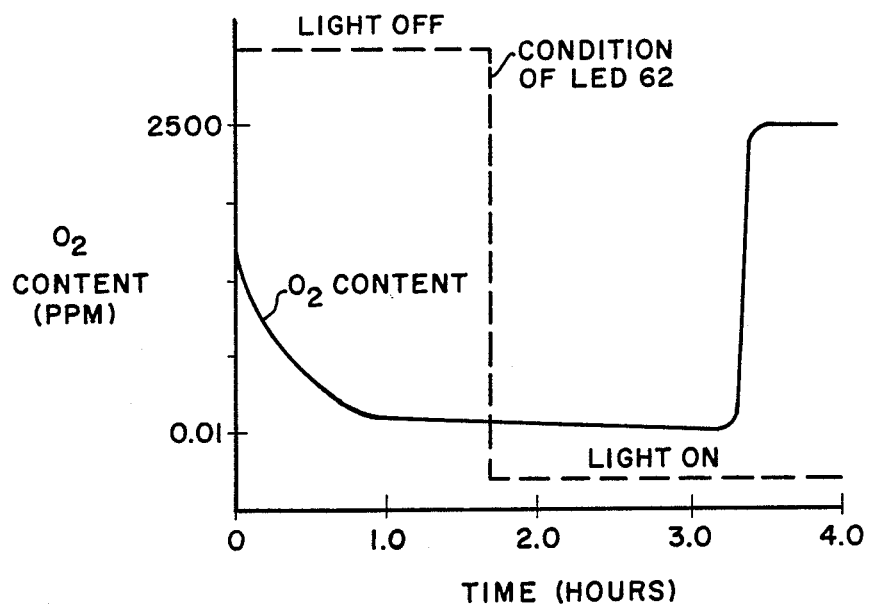
Fig_6

OPTOELECTRONIC CHEMICAL REACTION DETECTOR

BACKGROUND OF THE INVENTION

1. Field of the Invention

The present invention relates generally to optoelectronic detectors and more specifically to fiber optic detectors for detecting the presence of a chemical reaction.

2. Description of the Prior Art

Chemical reactions are critical to many processes in industry. Often the chemicals involved are hazardous and/or must be used at high pressures in sealed containers. When the reactions take place in the sealed containers, the human operator cannot directly determine if the chemical reaction is complete. The operator must estimate when the reaction has been completed and new chemicals added to replace the exhausted reactants.

One example involves the purification of gases. Many industries, such as the semiconductor industry, require high purity gases. To obtain this high purity, the gases must be passed through a chemical purifier which removes unwanted gases, moisture and other impurities. The chemical purifier contains a chemical resin through which the gas is passed. The resin is usually in the form of small one millimeter size pellets.

As the gas passes through the container, the resin reacts with and absorbs the unwanted gases, moisture and impurities. The resin near the entrance opening in the purifier reacts and is exhausted first. Thereafter, successive layers of resin are used up, and the boundary between the reacted resin and the unreacted resin moves down the container like a wave until all of the resin is exhausted. The container must then be replenished with fresh resin.

In order to maintain a constant high purity level of gas, the resin in the purifier must be replaced before it is exhausted. However, the high pressures and hazardous gases make direct inspection of the resin impossible. In addition, due to variables, such as the flow rate and the initial level of impurity of the gas, it is difficult to estimate when to replace the resin. Operators either replace the resin long before it is fully spent or wait until a sharp increase in the level of gas impurity is noticed.

Thus, there is a need for a means to automatically determine when the resin nears exhaustion so that the resin may be replaced and the purity level of the gas in the system maintained.

SUMMARY OF THE PRESENT INVENTION

It is therefore an object of the present invention to provide a device which automatically senses when a reaction has taken place.

It is another object of the present invention to provide a device with fiber optic sensors which measures the reflectance of a chemical resin.

Briefly, in a preferred embodiment, the present invention includes a reactant container for holding the chemical reactants. A tube extends inside a container having a transparent bulb sealed about its end. A fiber optic probe containing a transmitting fiber optic cable and a receiving fiber optic cable is positioned inside the tube such that the ends of the fiber optic cables are proximate to the inner surface of the bulb.

The fiber optic cables are connected to a fiber optic transmitter and receiver. The fiber optic transmitter and receiver transmits a light beam down the transmitting fiber optic cable. The light beam passes through the bulb, and is then reflected by the chemical reactants. The receiving fiber optic cable receives the reflected light and returns it to the fiber optic transmitter and receiver. The fiber optic transmitter and receiver compares the intensity of the reflected light received with the intensity of the original transmitted light. The fully reacted chemicals have a different reflectance value than the fresh chemicals, so when the reaction has taken place next to the bulb, the fiber optic transmitter and receiver will sense the change. Upon sensing a change, the fiber optic transmitter and receiver will activate a warning device, such as a light, which informs the operator that the reaction has been completed and the chemicals need replacing.

It is an advantage of the present invention in that it provides a device which automatically senses when a chemical reaction has taken place.

It is another advantage of the present invention in that it provides a fiber optic sensor which measures the reflectance of a chemical resin.

These and other objects and advantages of the present invention will no doubt become obvious to those of ordinary skill in the art after having read the following detailed description of the preferred embodiment which is illustrated in the various drawing figures.

IN THE DRAWINGS

FIG. 1 is a cut-away front elevation view of apparatus pursuant to the present invention;

FIG. 2 is a side elevation view of the apparatus of FIG. 1;

FIG. 3 is a side elevation view of an optic well of FIG. 1;

FIG. 4 is a side elevation view of a fiber optic probe of FIG. 1;

FIG. 5 is an end view of the probe of FIG. 4; and

FIG. 6 is a graph showing an operational test of the invention.

DETAILED DESCRIPTION OF THE PREFERRED EMBODIMENT

FIGS. 1 and 2 respectively show a cut-away front elevation view and a side elevation view, of a gas purification system using the reaction sensing device of the present invention and is designated by the general reference number 10. A pipe connector 12 is attached to a valve assembly 14. Valve assembly 14 is connected to a mounting plate 16. Valve assembly 14 is connected to an entrance pipe 18 which in turn is connected to a first end of a cylindrical container 20.

The container 20 is mounted to the plate 16 by means of a mounting strap 22. An intermediate pipe section 24 is connected near the second end of container 20. Pipe section 24 is connected to a filter 26 by means of a pipe connector 28. Filter 26 is in turn connected to an exit pipe section 30 by means of a connector 32. A valve assembly 34 is connected to the pipe section 30 and a connector 36. Valve assembly 34 is attached to mounting plate 16. Valve assemblies 14 and 34 allow the flow of gas through system 10 to be shut-off when system 10 has to be isolated for maintenance.

Container 20 has a hollow stem section 40 connected to the second end section of container 20. Stem section 40 is attached to a threaded connector 42. An optic well section 44 is received by connector 42. The well section 44 has an inner tube section 46 which extends into container 20. A bulb 48 is attached to the end of section 46. Well section 44 also has an outer tube section 50 with an end section 52 at its end. A fiber optic probe 54 (not shown) is inserted through well section 44 such that its end abuts bulb 48. A potted seal is formed behind probe 54.

The fiber optic probe 54 contains a transmitting fiber optic cable 56 and a receiving fiber optic cable 58. Cables 56 and 58 are attached to a fiber optic transmitter and receiver (FOTR) 60. The Banner Engineering Corporation of Minneapolis, Minn. and the Takenaka Corporation of Japan, both make FOTRs which could be used in the present invention. The FOTR is connected to a light emitting diode 62.

FIG. 3 shows a more detailed view of the optic well section 44. Section 44 is comprised of the bulb 48, inner tube section 46, a thread screw section 70, outer tube section 50 and end section 52. Sections 46, 50, 52 and 70 are all constructed of stainless steel and have a passage 72 running through their lengths. The inner diameter of passage 72 increases in the end section 52 to provide space for inserting the potted secondary seal.

Bulb 48 is made of a heat-resistant and chemical-resistant glass, e.g., Pyrex 7740. The bulb 48 is attached to the stainless steel section 46 by means of a glass to metal high vacuum seal at 1000° C. temperature. This seal actually attaches the glass to the outer oxide layer of the metal of section 46. Other types of high pressure glass seals could also be used.

FIG. 4 shows a side elevation view of the fiber optic probe 54. The probe 54 consists of a cylindrical guide bar section 80 and a locating member 82. Locating member 82 consists of a tab member which extends a distance of approximately 0.050 inches from the end of the bar section 80. Fiber optic cables 56 and 58 run along the length of section 80.

FIG. 5 shows an end view of the probe 54. The guide bar section 80 has a channel 90 running along its entire length. The channel 90 contains the two fiber optic cables 56 and 58 which are held in place by an adhesive 92. The cables 56 and 58 are mounted side-by-side in channel 90 such that they do not both lie along the same diametric line of the cylindrical guide bar section 80.

Probe 54 is sized to fit inside passage 72 of optic well section 44. The locating member 82 insures that the ends of the optic cables 56 and 58 do not touch the inner surface of the glass bulb 48. This is to prevent the glass bulb from reflecting the light of the transmitting cable 56 directly back to the receiving cable 58, without allowing the light to first pass outside bulb 48. For the same reasons, the cables 56 and 58 are located side-by-side, not along the same diametric line such that they are positioned in different radial sections of cylindrical probe 54, and are also offset from the center of guide bar section 80. Once the probe 54 is positioned inside optic well 44, a potted seal is formed behind probe 54 inside passage 72 and terminates inside section 52.

Referring again to FIG. 1, the operation of the invention may now be understood. Container 20 is filled with a purifying resin, e.g. Nanochem resin. Nanochem is a registered trademark. The purifying resin absorbs oxygen, moisture and other impurities in various gases.

Once the container 20 is filled with resin, the optic well section 44 is mated with the threaded connector 42. The optic probe 54 has previously been mounted and sealed within the optic well section 42. The fiber optic cables 56 and 58 are connected to the FOTR 60.

The valves 14 and 34 are opened and gas, such as nitrogen, begins to flow through system 10. The gas passes through the purifying container 20, the filter 26 and exits through connector 36. The resin in container 20 reacts with and absorbs the impurities in the gas. The resin near entrance pipe 18 reacts and is exhausted first and as more resin reacts, the boundary between the reacted and unreacted resin moves toward bulb 48.

The FOTR 60 sends a light beam down the transmitting fiber optic cable 56. The light exits the end of the cable 56 and passes through bulb 48. Some of the light is then reflected by the surrounding unreacted resin and enters bulb 48 where it is received by the receiving cable 58 and sent to the FOTR 60. The FOTR 60 compares the intensity of light received by cable 58 with the intensity of the light sent via cable 56. The intensity of the light reflected and returned to the FOTR 60 is much less than half the intensity of the light sent for unreacted resin.

The reflectivity of the resin changes once it reacts and is exhausted. In the case of Nanochem resin, the used resin is much more reflective. The resin will return reflected light to the FOTR 60 which is approximately one-half the light intensity of the light sent. The gain of the FOTR 60 is set so that when this level of light intensity is reached, a signal is sent and the LED 62 is lit. The LED 62 lets the operator know that the resin must be changed.

The length of section 46 can be configured to change the position of bulb 48 in container 20. This allows the amount of warning time, the period between the time the LED 62 goes on and the resin is exhausted, to be set to the particular user's needs. Someone who uses high flow rates would need to have a larger reserve of unused resin and would want a long section 46. Someone with very low flow rates could get by with a smaller amount of unreacted resin and would have a shorter section 46, and thus, a shorter warning time. In the usual case, the bulb is positioned to give the operator a five-day warning.

The reflectivity of different resins varies. However, the FOTR 60 can be adjusted for various other types of resin by adjusting the gain. This can be easily done by testing a sample of the reacted and unreacted resin with the probe 54. The gain of FOTR 60 is adjusted until the difference is detected.

FIG. 6 shows a graph of an accelerated test of the present invention. In this test, variables such as flow rate, impurity level and container size were adjusted so that the resin would be exhausted relatively quickly. For example, nitrogen with a known impurity level of 2,500 parts per million was passed through system 10. In most applications, an impurity level of four to five parts per million is normal. The flow rate was 0.5 liters per minute. The container 20 was filled with Nanochem resin which absorbs oxygen, as well as other impurities. As the test started, the oxygen level dropped off quickly to around 0.01 parts per million. After several hours, the resin was exhausted and the oxygen content rose back up to 2,500 parts per million.

In this test, the length of section 46 was such that bulb 48 was positioned in approximately the middle of container 20. As the graph shows, the light from LED 62 came on at approximately the half-way mark during the test. There was still over one and one-half hours of unreacted resin left. It would have been possible to adjust the bulb 48 to give as little as fifteen minutes of warning time. It should be noted, that during this test, the system 10 was run continuously at a very high flow rate and high impurity rate. In actual operation, the flow rate would be much less and not closely controlled. Under such circumstances, the operator would have a much longer warning time.

In applications involving gas purification, the gases are sometimes dangerous and potentially under high pressures. At typical pressures, usually one hundred psi, the seal between the bulb 48 and section 46 is critical. The present seal has been tested up to four thousand psi and thus provides a good safety margin. Also, the present invention provides a secondary potted seal.

Other embodiments of the present invention are possible. For example, the locating member 82 of FIG. 5 could have a different geometry, such as a cylindrical pin. Also, instead of having a channel 90, separate passages could be bored through guide bar 80 for cables 56 and 58.

The present invention can be used in other applications. One such application involves detecting the amount of liquified gas remaining in a container. By adjusting the gain of the FOTR and the position of the bulb in the container, the present invention could detect when the level of liquid gas has dropped below a certain point.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. An optoelectronic chemical reaction detector comprising:
    a pressurized container having chemical reactants;
    a transparent member hermetically sealed within a wall of the container for allowing passage of light into and out of the container; and
    an optic transmitter and receiver positioned proximate the transparent window and in optical communication with said chemical reactants, for transmitting a light beam to said chemical reactants and comparing the intensity of said light beam as originally transmitted with the intensity of said light beam after being reflected off of said chemical reactants.

2. The device of claim 1 wherein,
    a light conducting means is connected intermediate to and with the optic transmitter and receiver and the transparent member.

3. An optoelectronic chemical reaction detector comprising:
    a pressurized container having a supply of chemical reactants;
    a tube extending through and into the interior of the container;
    a transparent member hermetically sealed to the end of the tube and adjacent to said chemical reactants;
    a fiber optic probe positioned inside the tube and having a transmitting fiber optic cable and a receiving fiber optic cable, each of said cables terminating adjacent the transparent member such that each is in optical communication with said chemical reactants through the transparent member; and
    a fiber optic transmitter and receiver connected to said transmitting fiber optic cable and said receiving fiber optic cable for transmitting a light beam along said transmitting fiber optic cable to said reactants and comparing the intensity of said light beam as originally transmitted with the intensity of said light beam as received from said receiving fiber optic cable after being reflected off of said chemical reactants.

4. The device of claim 3 wherein,
    the fiber optic probes has a locating member extending from one end with said locating member abutting an inside surface of the transparent member such that said transmitting and receiving fiber optic cables are off-set a distance from the surface of the transparent member.

5. The device of claim 3 wherein,
    the transparent member is bulb shaped.

6. The device of claim 5 wherein,
    the fiber optic probe has a channel running along its length for receiving said transmitting fiber optic cable and said receiving fiber optic cable.

7. The device of claim 6 wherein,
    said channel is off-set from a centerline of said probe.

8. The device of claim 5 wherein,
    the fiber optic probe is cylindrical and said transmitting fiber optic cable and said receiving fiber optic cable are positioned with each one oriented in a different radial section of the fiber optic probe.

9. The device of claim 3 further including,
    a light emitting device connected to the fiber optic transmitter and receiver for receiving a signal from the fiber optic transmitter and receiver and emitting light in response thereto.

10. The device of claim 3 further including,
    a potted seal between the fiber optic probe and the tube.

11. The device of claim 3 wherein,
    said chemical reactants are nontransparent.

12. The device of claim 3 wherein,
    said chemical reactants comprise a gas purifying resin of solid particles; and
    the container has a gas inlet for receiving a flow of pressurized gas, and a gas outlet for transmitting a flow of pressurized gas, the transparent member being located intermediate said gas inlet and said gas outlet.

13. A method for detecting a chemical reaction comprising the steps of:
    filling a pressurized chamber with chemical reactants;
    hermetically sealing a transparent member over an aperture in said chamber;
    positioning a first end of a transmitting fiber optic cable adjacent said transparent member and connecting a second end to a fiber optic transmitter and receiver;
    positioning a first end of a receiving fiber optic cable adjacent said transparent member and connecting a second end to said fiber optic transmitter and receiver;
    operating said fiber optic transmitter and receiver to send a beam of light along said transmitting fiber optic cable and through said transparent member and hitting said chemical reactants to produce reflected light;
    receiving said reflected light in said receiving fiber optic cable and delivering said reflected light to said fiber optic transmitter and receiver; and operating said fiber optic transmitter and receiver to compare the intensity of the beam of light as originally transmitted with intensity of the reflected light in order to determine if said chemical reactants have fully reacted.

14. The method of claim 13 further including the step of, operating said transmitter and receiver such that said transmitter and receiver sends a warning signal to an operator warning device when said reflected light indicates that said chemical reactants have fully reacted.

15. The method of claim 13, wherein, said chemical reactants are nontransparent.

* * * * *